(12) United States Patent
Okubo et al.

(10) Patent No.: US 9,872,665 B2
(45) Date of Patent: Jan. 23, 2018

(54) CATHETER

(71) Applicant: TERUMO KABUSHIKI KAISHA, Shibuya-ku (JP)

(72) Inventors: Itaru Okubo, Ninomiya (JP); Haruhiko Kamijo, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 702 days.

(21) Appl. No.: 14/477,486

(22) Filed: Sep. 4, 2014

(65) Prior Publication Data

US 2014/0371598 A1    Dec. 18, 2014

Related U.S. Application Data

(63) Continuation of application No. PCT/JP2013/056237, filed on Mar. 7, 2013.

(30) Foreign Application Priority Data

Mar. 9, 2012   (JP) .................................. 2012-053713

(51) Int. Cl.
*A61B 8/00*    (2006.01)
*A61B 8/12*    (2006.01)
(Continued)

(52) U.S. Cl.
CPC ............ *A61B 8/445* (2013.01); *A61B 8/0891* (2013.01); *A61B 8/12* (2013.01); *A61B 5/0066* (2013.01);
(Continued)

(58) Field of Classification Search
CPC .... A61B 5/05; A61B 8/00; A61B 5/14; A61B 6/00; A61B 8/12; A61B 8/445
See application file for complete search history.

(56) References Cited

U.S. PATENT DOCUMENTS 4,795,434 A      1/1989  Kujawski
2007/0232892 A1* 10/2007  Hirota .................. A61B 5/0066
                                                      600/407
(Continued)

FOREIGN PATENT DOCUMENTS

EP    2364746 A1    9/2011
JP    2002-360578 A  12/2002
(Continued)

OTHER PUBLICATIONS

International Search Report (PCT/ISA/210) dated Apr. 2, 2013, by the Japanese Patent Office as the International Searching Authority for International Application No. PCT/JP2013/056237.
(Continued)

*Primary Examiner* — Joel Lamprecht
(74) *Attorney, Agent, or Firm* — Buchanan Ingersoll & Rooney PC (57) ABSTRACT

A catheter including a sheath configured to be inserted into a lumen; a drive shaft inserted into the sheath; an image information acquiring unit fixed to a distal end of the drive shaft and acquires image information; a hub which moves the drive shaft in an axial direction of the sheath; an outer tube on a proximal end side of the sheath and includes a first connector at a proximal end thereof; a second connector which includes on a proximal end side of the outer tube a male connector able to be connected to and disconnected from the first connector; and an inner tube on a distal end side of the hub, that moves with respect to the outer tube along with the movement of the hub, and includes at a distal end thereof a latch section that is not able to pass through the second connector.

21 Claims, 10 Drawing Sheets

(51) Int. Cl.
   *A61B 8/08*     (2006.01)
   *A61B 5/00*     (2006.01)
   *A61M 25/00*    (2006.01)

(52) U.S. Cl.
   CPC ............... *A61M 2025/0004* (2013.01); *A61M 2025/0006* (2013.01)

(56) References Cited

U.S. PATENT DOCUMENTS

| | | |
|---|---|---|
| 2007/0232893 A1 | 10/2007 | Tanioka |
| 2009/0156941 A1 | 6/2009 | Moore |
| 2011/0224650 A1 | 9/2011 | Itou et al. |

FOREIGN PATENT DOCUMENTS

| | | |
|---|---|---|
| JP | 2007-268133 A | 10/2007 |
| JP | 2011-067537 A | 4/2011 |
| JP | 2011-152274 A | 8/2011 |
| JP | 2011-188913 A | 9/2011 |
| WO | WO 99/15078 A1 | 4/1999 |
| WO | 2013/146259 A1 | 10/2013 |

OTHER PUBLICATIONS

Extended European Search Report dated Sep. 24, 2015 by the European Patent Office in counterpart European Application No. 13757920.7. (5 pages).

\* cited by examiner

CATHETER

CROSS-REFERENCES TO RELATED APPLICATIONS

This application is a continuation of International Application No. PCT/JP2013/056237 filed on Mar. 7, 2013, and claims priority to Japanese Application No. 2012-053713 filed on Mar. 9, 2012, the entire content of both of which is incorporated herein by reference.

TECHNICAL FIELD

The disclosure here relates to a catheter, and more particularly to a catheter which is inserted into a lumen such as a blood vessel or a vascular channel to capture an image in the lumen.

BACKGROUND DISCUSSION

In order to examine a target lesion in a lumen such as a blood vessel or a vascular channel, an ultrasonic catheter which transmits and receives ultrasonic waves to and from the target lesion is used. The ultrasonic catheter is provided with an imaging core which includes an oscillator unit for transmitting and receiving the ultrasonic waves and a drive shaft for rotating the oscillator unit, and a sheath which incorporates the imaging core and is inserted into the lumen. The imaging core can move in an axial direction in the sheath.

When the ultrasonic catheter is used, an introducer sheath for accessing the lumen is typically indwelled, and a guiding catheter is inserted into the lumen via the introducer sheath. Thereafter, a guide wire is inserted up to a targeted portion via the guiding catheter, and the ultrasonic catheter is inserted into a deeper portion than the target lesion along the guide wire. Then, only the imaging core is made to retreat such that the imaging core is arranged on a distal end side in the sheath, while the sheath is made to pass through the target lesion. Since the oscillator unit moves from the deeper portion and passes through the target lesion by causing only the imaging core to retreat, it is possible to observe ultrasonic images which are successively acquired before and after the target lesion and to create three-dimensional data with a shape of the blood vessel or the vascular channel.

In order to enable the imaging core to move in the axial direction in the sheath, an ultrasonic catheter disclosed in International Publication No. 1999/015078, for example, includes a nested structure which expands and contracts in the axial direction and is provided on a proximal end side, and the imaging core in the sheath is made to move in the axial direction with respect to the sheath by changing an entire length of a main body of the catheter.

In addition, the ultrasonic catheter disclosed in International Publication No. 1999/015078 includes a connection section which is provided between the sheath and the nested structure and can be connected and disconnected, and it is possible to pull out the imaging core from the main body of the catheter in accordance with a particular situation.

There is a case where the ultrasonic catheter, as disclosed in International Publication No. 1999/015078, is caught by a complicatedly curved blood vessel or a narrowed blood vessel or with a stent or the like which is embedded in a blood vessel, and is brought into a situation where it is difficult to pull out the ultrasonic catheter from the blood vessel. It is considered to facilitate easier pulling-out of the sheath by removing the imaging core from the sheath in such a case.

However, if pulling out the imaging core of the ultrasonic catheter disclosed in International Publication No. 1999/015078 is attempted, the connection section approaches a Y connector, which is connected on a proximal end side of the guiding catheter in a state where the ultrasonic catheter is inserted into the guiding catheter since the connection section is provided between the sheath and the nested structure. Since the guide wire also comes from the Y connector, there is a concern that the guide wire and the connection section may interfere with each other and it may become difficult to push the guide wire when the ultrasonic catheter is operated, which may deteriorate operability. Furthermore, since the connection section approaches the Y connector, there is a concern that blood flowing out from the connection section after the imaging core is extracted may be confused with blood flowing out from the Y connector, which may cause an erroneous operation. Furthermore, since the connection section approaches the Y connector, the blood flowing out from the connection section flows into a valve body, which is provided in the Y connector, from outside, which also may deteriorate operability.

SUMMARY

The disclosure herein addresses the aforementioned problems, and provides a catheter which exhibits high operability while including parts which can be connected and disconnected.

A catheter according to an exemplary embodiment of the disclosure includes: a sheath which is configured to be inserted into a lumen; a drive shaft which is inserted into the sheath and delivers mechanical drive force; an image information acquiring unit which is fixed to a distal end of the drive shaft and acquires image information; a hub which moves while holding the drive shaft and thereby moves the drive shaft in an axial direction of the sheath; an outer tube which is provided on a proximal end side of the sheath and includes a first connector at a proximal end thereof; a second connector, which is able to be connected to and disconnected from the first connector, on a proximal end side of the outer tube; and an inner tube which is provided on a distal end side of the hub, moves with respect to the outer tube in the outer tube along with the movement of the hub, and includes a latch section with an enlarged outer diameter provided at a distal end thereof, wherein the second connector includes a passing port which can receive the inner tube, and the passing port has an opening diameter which does not allow the latch section to pass therethrough.

The catheter configured as described above has a configuration in which the second connector provided on the proximal end side of the outer tube can be disconnected, and the second connector is arranged so as to be separate from an insertion target such as a Y connector during an operation. For this reason, it becomes possible to disconnect the second connector without causing the second connector to interfere with the guide wire, which extends from the insertion target, even when it is difficult to pull out the catheter in a blood vessel. It also becomes easier to push the guide wire located at a separate position, and operability of the guide wire and the catheter is thereby enhanced. In addition, since the second connector is separated from the insertion target, with the outer tube interposed therebetween, erroneous recognition of blood flowing out from the second connector as blood flowing out from the insertion target occurs less often. It thus becomes possible to perform operations while checking from which of the second connector and the insertion target the blood flows out from, and therefore, the operability is enhanced. In addition, since the second connector is separate from the insertion target, with the outer tube interposed therebetween, blood flowing out from the second connector from the outside and entering into the insertion target occurs less often, and operability is further enhanced.

In addition, if the first connector and the second connector are screw-in connectors, it is possible to easily connect and disconnect the first connector and the second connector, and the operability is enhanced.

Further, if the second connector includes a seal member which is brought into contact with an outer circumferential surface of the inner tube so as to be able to slide, it is possible to move the inner tube with respect to the second connector, to easily connect and disconnect the second connector to be able to rotate independently from both the outer tube and the inner tube, and to suppress leakage from a part between the second connector and the inner tube.

DETAILED DESCRIPTION

Hereinafter, a description will be given of an exemplary embodiment of the disclosure with reference to the drawings. The dimensional ratios in the drawings are drawn with exaggeration for convenience of understanding the description and differ from actual ratios.

Figure 1:
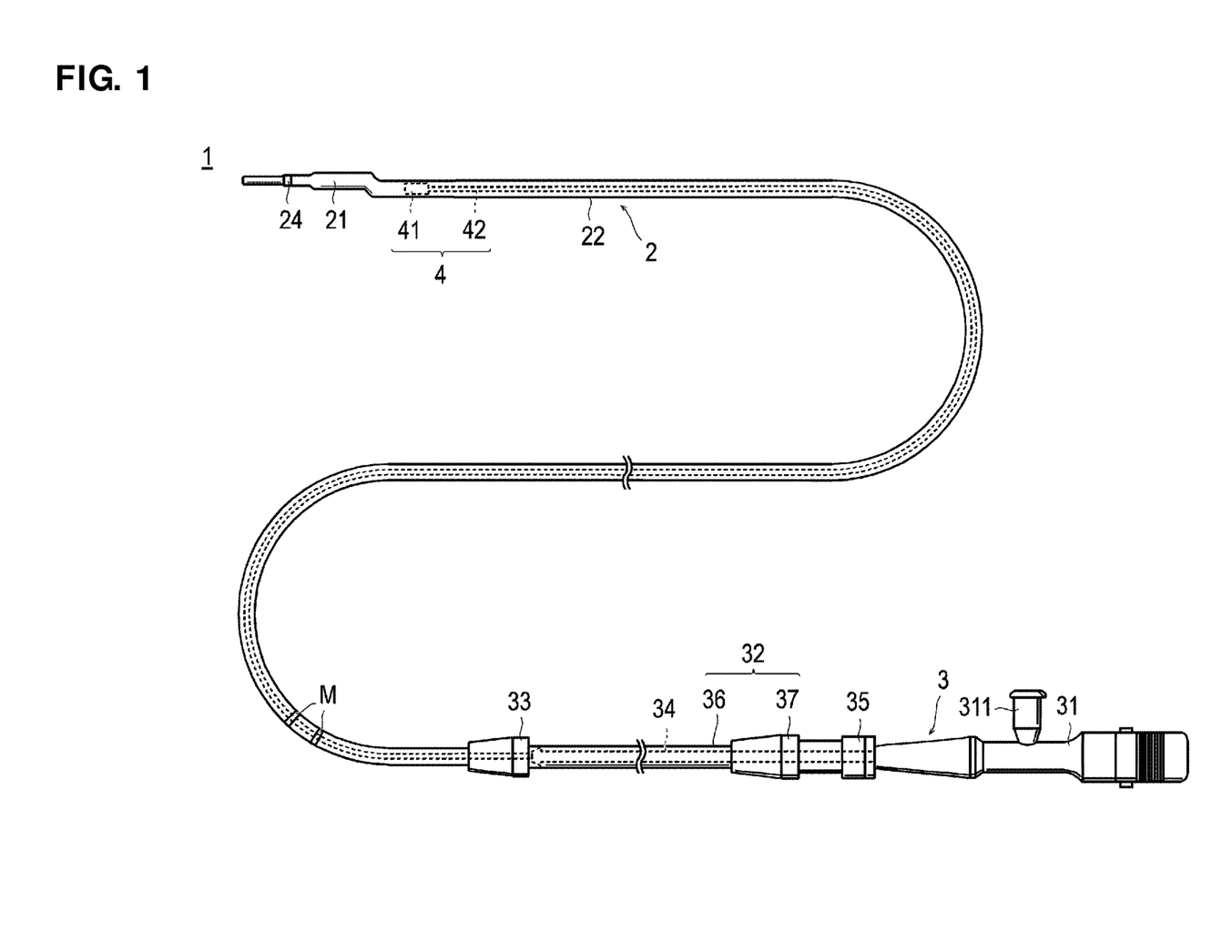
FIG. 1 is a planar view showing an ultrasonic catheter according to an exemplary embodiment of the disclosure herein.
Figure 2:
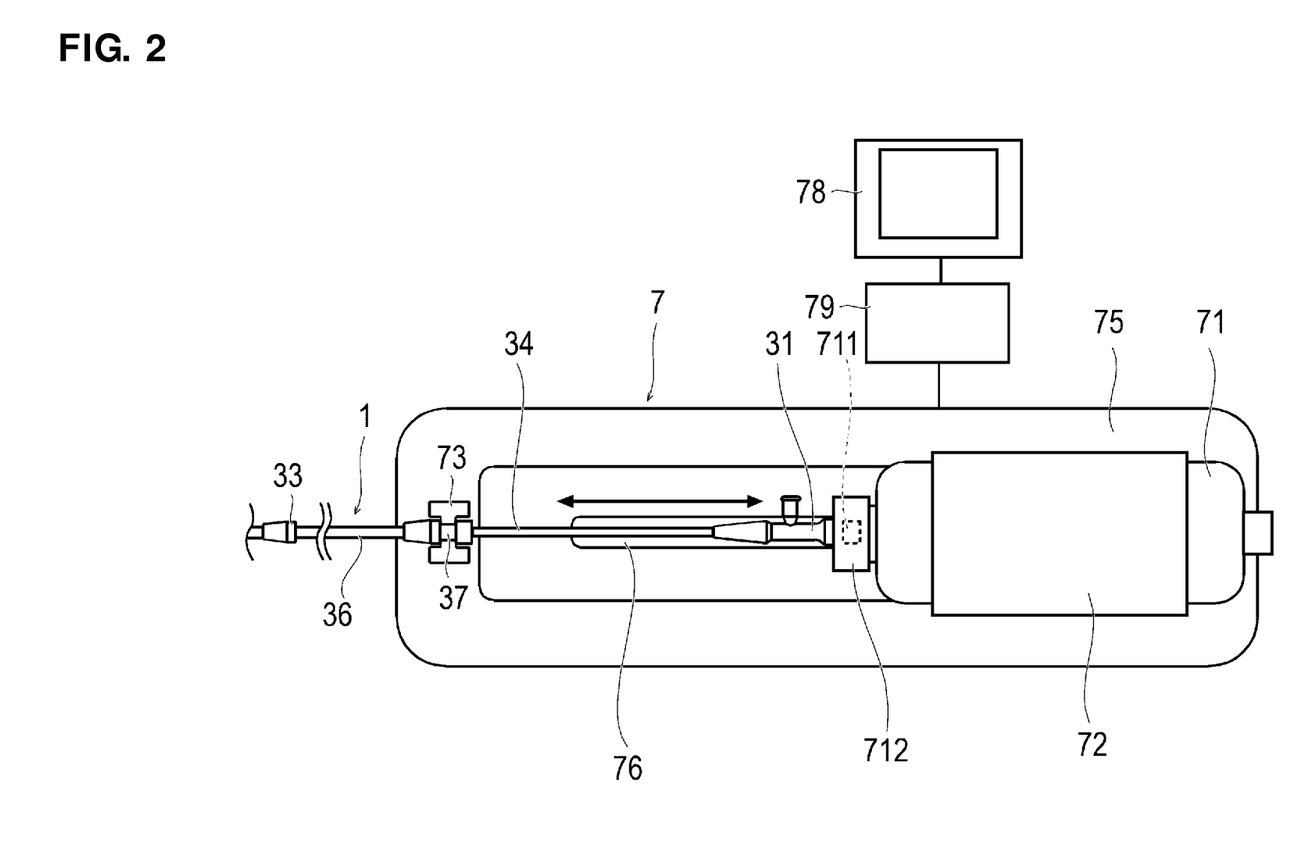
FIG. 2 is a schematic planar view showing an intraluminal diagnosis system which is provided with the ultrasonic catheter according to the exemplary embodiment of FIG. 1.

A catheter according to the exemplary embodiment is an ultrasonic catheter 1 which is inserted mainly into a blood vessel and makes diagnosis on the inside of the blood vessel based on an image, and accommodates an imaging core 4, which is for ultrasonic diagnosis, as shown in FIG. 1. The ultrasonic catheter 1 is used while connected to an external drive apparatus 7 which holds the ultrasonic catheter 1 and drives the imaging core 4 as shown in FIG. 2. In the disclosure here, a side, on which the ultrasonic catheter 1 is inserted into a lumen, will be referred to as a "distal end" or a "distal end side", and a side, on which the ultrasonic catheter 1 is operated, will be referred to as a "proximal end" or a "proximal end side".

As shown in FIG. 1, the ultrasonic catheter 1 is provided with a sheath 2 which is inserted into a lumen, an imaging core 4 which transmits and receives ultrasonic waves to and from tissues in the lumen, and an operation unit 3, through which the imaging core 4 extends, and which is positioned on a further proximal end side than the sheath 2.

The sheath 2 includes a sheath distal end 21, a sheath tube 22, and a filling fluid inlet and outlet path member 23.

Figure 3:
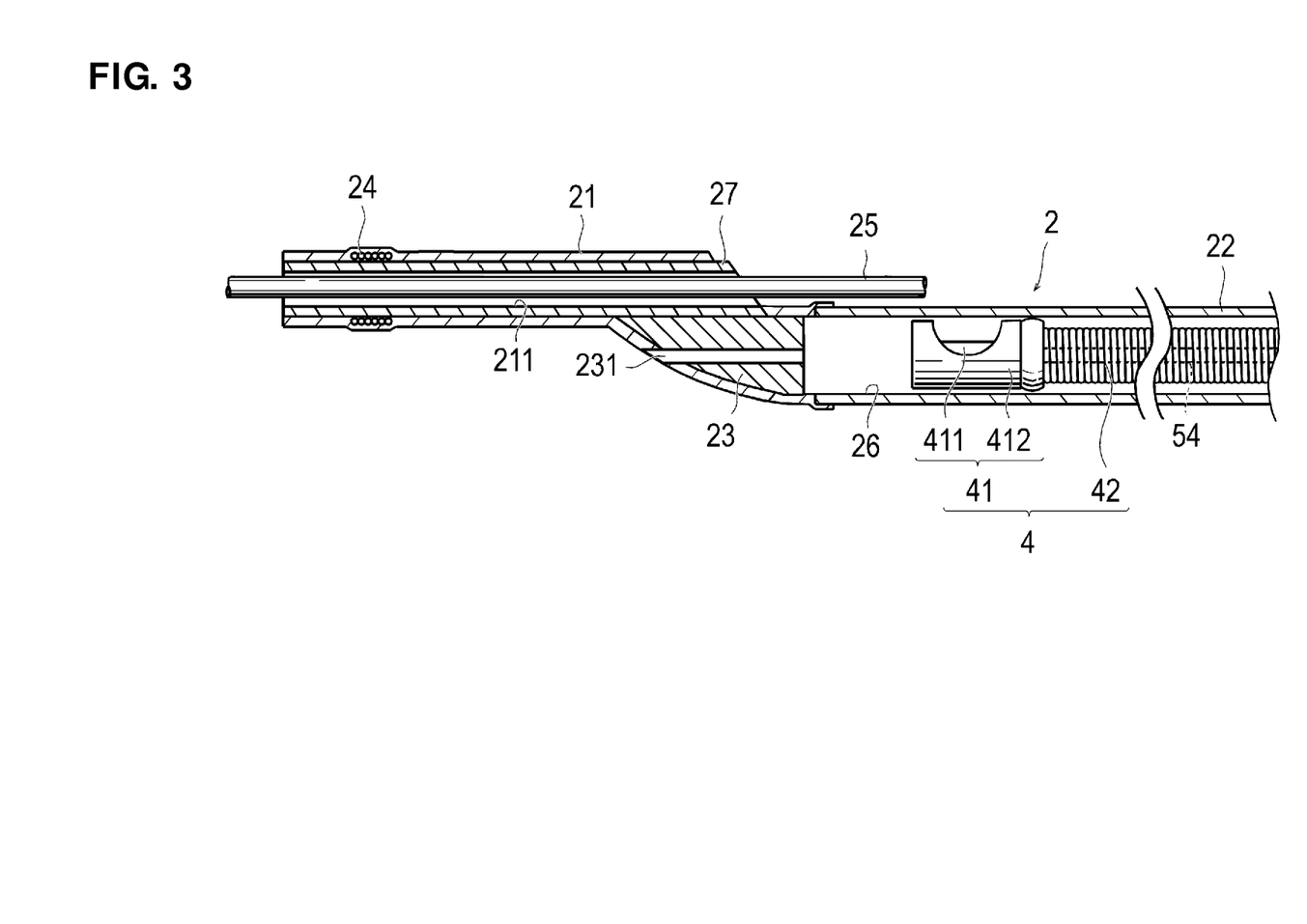
FIG. 3 is a longitudinal-direction cross-sectional view showing a distal end of the ultrasonic catheter according to the exemplary embodiment of FIG. 1.

The sheath distal end 21 includes a tubular sheath distal end member 27 with a guide wire lumen 211 formed therein and an X-ray contrast marker 24 provided at a portion on a slightly further proximal end side than the distal end. The guide wire 25 is inserted into a lumen in advance, and the ultrasonic catheter 1 is guided up to the target lesion while the guide wire 25 is made to pass through the guide wire lumen 211. The X-ray contrast marker 24 is provided so as to be able to check a position of the distal end of the ultrasonic catheter 1 under X-ray fluoroscopic guidance when inserted into the lumen. The ultrasonic catheter 1 has a "rapid exchange structure" in which the guide wire lumen 211 is provided only at the distal end, and according to the structure, the guide wire lumen 211 is not present within an imaging range of the imaging core 4 such that the guide wire lumen 211 does not inhibit imaging.

In the filling fluid inlet and outlet path member 23, a priming port 231 is formed, which is a hole in communication with a lumen 26 in the sheath tube 22 for causing a physiological salt solution filling the sheath tube 22 to flow to the outside.

In the sheath 2, the imaging core 4 is incorporated so as to be able to slide in the axial direction of the sheath 2. The imaging core 4 includes an oscillator unit 41 for transmitting and receiving ultrasonic waves to and from tissue in the lumen and a drive shaft 42, to which oscillator unit 41 is attached at the distal end thereof and which rotates the oscillator unit 41. The oscillator unit 41 includes an ultrasonic oscillator 411 (image information acquiring unit) for transmitting and receiving ultrasonic waves and a housing 412 which accommodates the ultrasonic oscillator 411 therein. The oscillator is also called a "transducer."

The sheath tube 22 is formed from a material with high ultrasonic wave permeability. A portion of the sheath tube 22, within which the ultrasonic oscillator 411 moves, includes an acoustic window section through which the ultrasonic waves penetrate. A marking section M is provided on the surface of the sheath tube 22 such that an operator can visually recognize a length, by which the sheath 2 is pushed into the lumen.

The drive shaft 42 is flexible such that it is possible to deliver rotational power which acts on the operation unit 3 from the external drive apparatus 7 (see FIG. 2) to the oscillator unit 41. The drive shaft 42 is configured of a multilayer coil-shaped tubular body such as a three-layer coil in alternate winding directions, for example, in the right, left, and right directions. The oscillator unit 41 is rotated by the drive shaft 42 delivering the power of rotation, and a target lesion in a lumen such as a blood vessel or a vascular channel can be observed by 360°. In addition, the drive shaft 42 includes a signal line 54 inserted therein for delivering a signal detected by the oscillator unit 41 to the operation unit 3.

The operation unit 3 includes a hub 31 which has a port 311 for inletting a physiological salt solution and for air venting, an outer tube 32 which is provided and fixed on the proximal end side of the sheath 2, a relay connector 33 which connects a portion between the outer tube 32 and the sheath 2, and a second connector 35 which can be connected to or disconnected from the proximal end side of the outer tube, and an inner tube 34 which is fixed on the distal end side of the hub 31 and moves with respect to the outer tube in the outer tube along with the movement of the hub 31. The outer tube 32 includes an outer tube main body 36 on the distal end side which is fixed to the relay connector 33 and a unit connector 37 which is fixed to the proximal end side of the outer tube main body 36 and can be connected to and disconnected from the second connector 35.

The hub 31 holds the drive shaft 42 and the inner tube 34. The inner tube 34 is pushed into or drawn out from the outer tube 32, which includes a unit connector 37 and an outer tube main body 36, and the drive shaft 42 slides in the operation unit 3 and the sheath 2 in the axial direction in conjunction with the inner tube 34.

When the inner tube 34 is pushed up to the deepest portion, an end portion of the inner tube 34 on the distal end side reaches the vicinity of an end of the outer tube 32 on the distal end side, namely the vicinity of the relay connector 33. In this state, the oscillator unit 41 is positioned in the vicinity of a distal end of the sheath tube 22 of the sheath 2.

Figure 4:
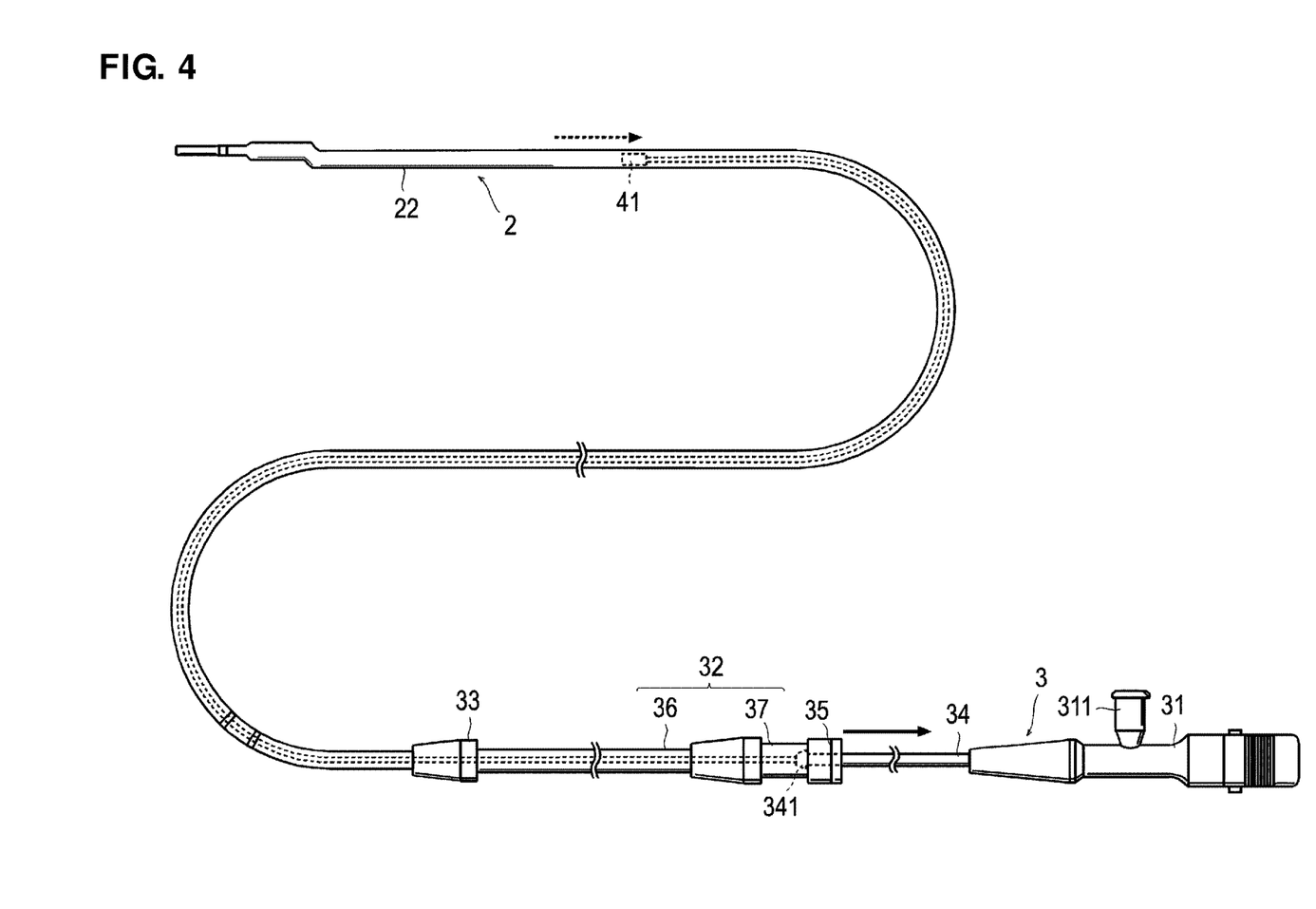
FIG. 4 is a planar view showing the ultrasonic catheter according to FIG. 1 when an oscillator unit is pulled back.

In addition, when the inner tube 34 is drawn out to the maximum extent, a stopper 341 (latch section), which is formed at the distal end such that the outer diameter increases, hooks an inner wall of the second connector 35, and a remaining part other than that in the vicinity of the hooked distal end is exposed, as shown in FIG. 4. In addition, the inside of the oscillator unit 41 is drawn back while the sheath 2 is left in place. By the oscillator unit 41 rotating and moving, it is possible to create a tomographic image of a blood vessel, a vascular channel, or the like.

Figure 5:
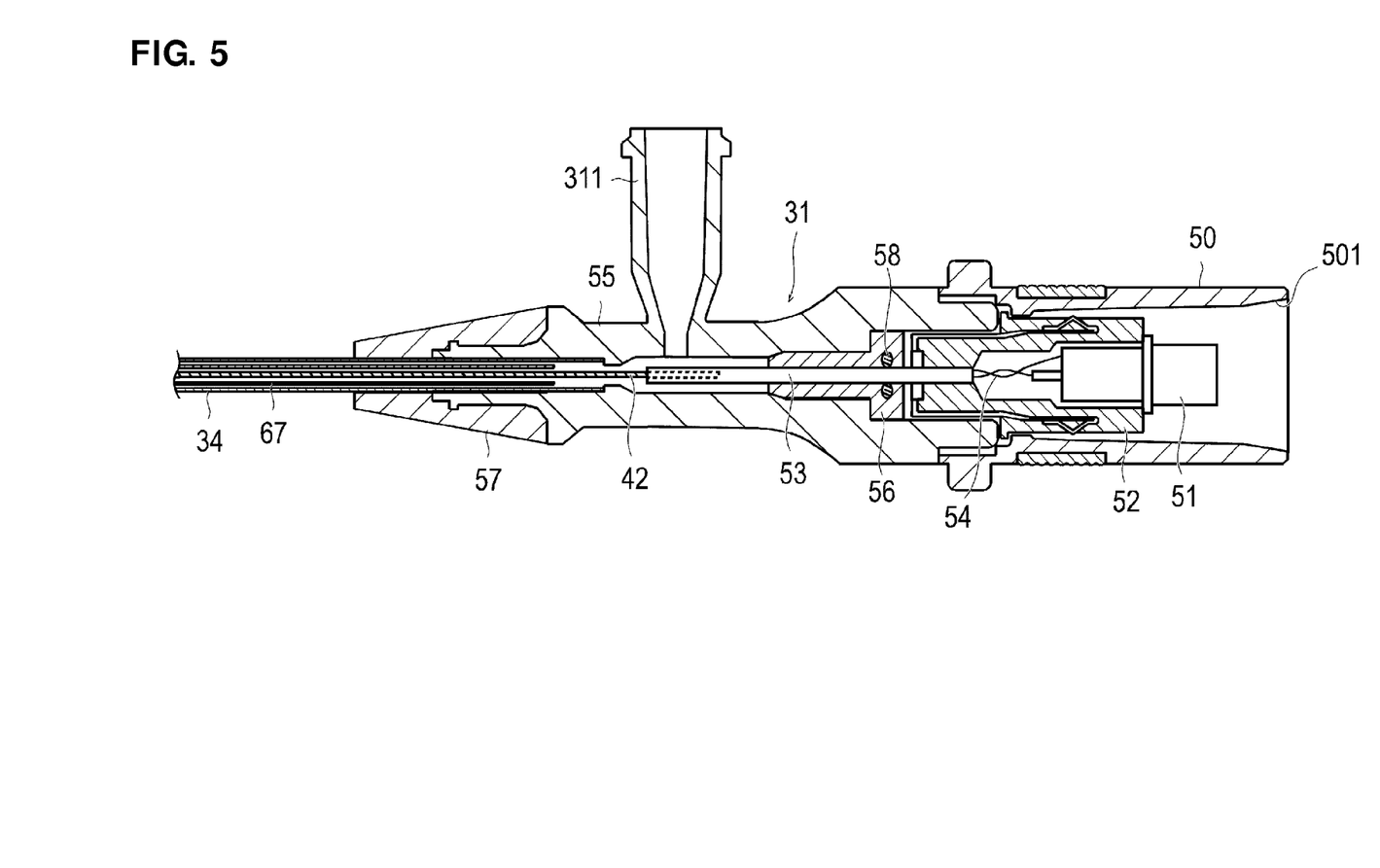
FIG. 5 is a longitudinal-direction cross sectional view showing a hub of the ultrasonic catheter according to the exemplary embodiment of FIG. 1.

The hub 31 of the operation unit 3 includes a joint 50, a drive male connector 51, a rotor 52, a connection pipe 53, a signal line 54, a hub main body 55, a sealing section 56, and a kink inhibiting protector 57, as shown in FIG. 5.

The joint 50 includes an opening 501 on a hand side of the operator of the ultrasonic catheter 1, and the drive male connector 51 and the rotor 52 are arranged therein. The drive male connector 51 can be coupled to a drive female connector 711 included in the external drive apparatus 7 (see FIG. 2) from the side of the opening 501 of the joint 50, and with such a configuration, the external drive apparatus 7 and the drive male connector 51 are mechanically and electrically coupled.

The rotor 52 is rotated integrally with holds the connection pipe 53 and the drive male connector 51. The connection pipe 53 holds the drive shaft 42 at an end on a side opposite to the rotor 52 in order to deliver rotation of the rotor 52 to the drive shaft 42. In addition, the rotor 52 is interposed between the joint 50 and the hub main body 55 such that movement thereof in the axial direction is restricted. The signal line 54 is made to pass through the inside of the connection pipe 53, and one end of the signal line 54 is connected to the drive male connector 51, and the other end is connected to the oscillator unit 41 after passing through the drive shaft 42. An observation result by the oscillator unit 41 is sent to the external drive apparatus 7 via the drive male connector 51, appropriate processing is performed thereon, and the observation result is displayed as an image.

A physiological salt solution is introduced into the hub main body 55 from the port 311, and the physiological salt solution is guided into the inner tube 34 without causing leakage to the outside. In addition, since the sealing section 56 includes an O-ring 58 installed between the hub main body 55 and the joint 50, the physiological salt solution does not cause leakage to the side of the opening 501 of the joint 50.

A part of the inner tube 34 is fitted into the hub main body 55, and the kink inhibiting protector 57 is arranged circumferentially on the inner tube 34 and the hub main body 55.

Figure 6:
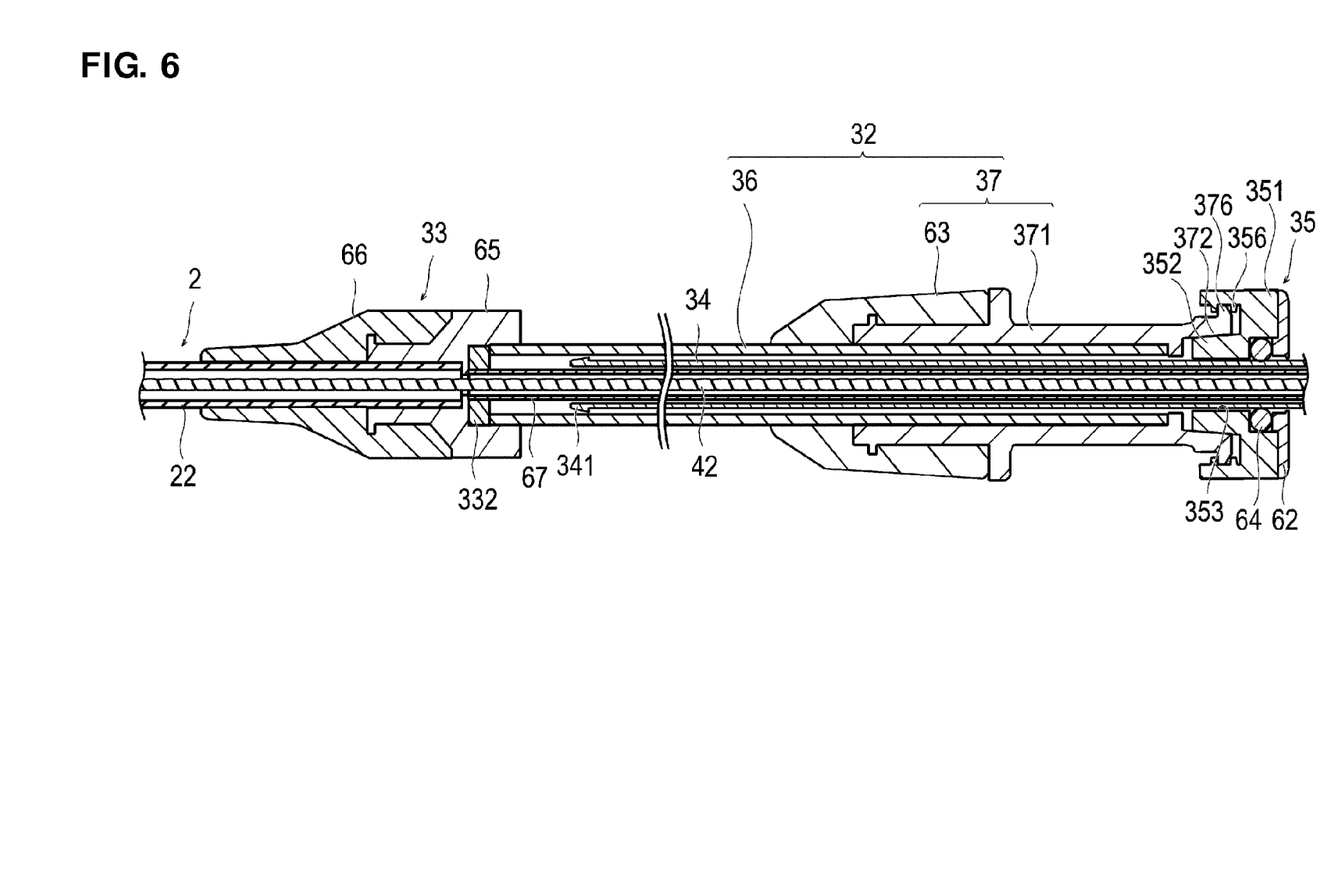
FIG. 6 is a longitudinal-direction cross sectional view showing a unit connector and a relay connector of the ultrasonic catheter according to the exemplary embodiment of FIG. 1.

The unit connector 37 includes a unit connector main body 371 and a cover member 63 as shown in FIG. 6. A tapered female connector 372 (first connector) and a male screw section 376 formed in an outer circumference of the female connector 372 are formed on the proximal end side of the unit connector main body 371.

The second connector 35 includes a connection section main body 351, a tapered male connector section 352 which can be connected to the female connector section 372 of the unit connector 37 in a liquid tight manner and disconnected therefrom, a female screw section 356 which is formed in an outer circumference of the male connector section 352, a proximal end sealing member 62, and a seal member 64 as an O-ring. The female connector 372 and the male connector section 352 have luer taper structures with predetermined gradients in order to exhibit a high sealing performance. The unit connector main body 371 and the second connector 35 are fixed to each other by screwing the male screw section 376 into the female screw section 356 and can fixedly maintain a state where the male connector section 352 is connected to the female connector section 372 in the liquid tight manner. That is, the female connector 372 and the male connector section 352 have locking-type luer taper structures with a screw-type locking mechanism configured on the male screw section 376 and the female screw section 356. The second connector 35 is provided with a passing port 353 through which the inner tube 34 can slide and extend through in a liquid tight manner. The passing port 353 has an opening diameter which is smaller than an outer diameter of the stopper 341, and the stopper 341 cannot pass therethrough. The proximal end sealing member 62 holds the seal member 64 in combination with the connection section main body 351. The seal member 64 is brought into contact with the outer circumferential surface of the inner tube 34 so as to be slidable and allows the second connector 35 to rotate in a circumferential direction with respect to the inner tube 34 and move in the axial direction. Since the seal member 64 is sealed, the physiological salt solution does not cause leakage to the outside from a portion between the second connector 35 and the inner tube 34 even if the physiological salt solution supplied to the port 311 of the hub 31 flows into the outer tube 32 through the inner tube 34.

The outer tube main body 36 attached to the relay connector 33 is inserted into and fixed to the unit connector main body 371, and the inner tube 34 extending from the hub 31 is inserted into the outer tube main body 36. The cover member 63 holds the outer tube main body 36 in combination with the unit connector main body 371.

Since the stopper 341 (latch section) is formed at the distal end of the inner tube 34 extending from the hub 31, the stopper 341 hooks the inner wall of the second connector 35, and the inner tube 34 is not pulled out from the unit connector 37 even if the hub 31 is drawn out to the maximum extent, that is, even if the inner tube 34 is drawn out from the outer tube 32 to the maximum extent.

The relay connector 33 includes an outer tube holding section 65 and a kink inhibiting protector 66. The outer tube holding section 65 holds the outer tube main body 36. In addition, an end of the sheath tube 22 on the proximal end side is coupled to an inner surface of the outer tube holding section 65. Although the sheath tube 22 has a one-layer structure in FIG. 6, the sheath tube 22 may have a multilayer structure.

A protecting tube 67 is fixed to an inner wall of an outlet member 332, through which the drive shaft 42 passes, in the outer tube holding member 65. The protecting tube 67 extends toward the inside of the inner tube 34 extending from the hub 31 and is arranged between the drive shaft 42 and the inner tube 34. Accordingly, when the inner tube 34 is pushed into the outer tube 32, the protecting tube 67 is pushed into the inner tube 34 in a direction opposite to the pushing direction. When the inner tube 34 is pushed into and drawn out from the outer tube 32, the protecting tube 67 is also relatively pushed into and drawn out from the inner tube 34 in the opposite direction, and therefore, it is possible to suppress bending force by the protecting tube 67 and to prevent kinks even if friction occurs due to contact with the inner tube 34 and the bending force occurs at the drive shaft 42. In addition, since the protecting tube 67 is formed by a metal coarsely wound coil-shaped tubular body and the physiological salt solution can flow thereinto through a gap in the coil for this reason, air does not remain in the outer tube 32.

The aforementioned ultrasonic catheter 1 is connected to and driven by the external drive apparatus 7 as shown in FIG. 2. The external drive apparatus 7 preferably includes a base table 75 having mounted thereon a drive unit 71 which incorporates an external drive source such as a motor and rotates and drives the drive shaft, moving means 72 for carrying the drive unit 71 and moving the drive unit 71 in the axial direction by the motor or the like, and a holding section 73 which holds a part of the ultrasonic catheter 1 in a fixed position manner. The external drive apparatus 7 is connected to a control unit 79 which controls the drive unit 71 and the moving means 72, and an image acquired by the oscillator unit 41 is displayed on a display unit 78 connected to the control unit 79.

The moving means 72 is a sending mechanism which can carry and fix the drive unit 71, and causes the carried and fixed drive unit 71 to advance back and forth along a groove rail 76 on the base table 75.

The drive unit 71 includes the drive female connector 711 to which the drive male connector 51 of the ultrasonic catheter 1 can be connected and a joint connection section 712 which can be connected to the joint 50 of the ultrasonic catheter 1, so as to enable transmission and reception of signals to and from the oscillator unit 41 and rotation of the drive shaft 42.

Ultrasonic scanning (scan) by the ultrasonic catheter 1 is performed by delivering rotation movement of the motor in the drive unit 71 to the drive shaft 42, rotating the housing 412 fixed to the distal end of the drive shaft 42, and scanning in a substantially radial direction, wherein the ultrasonic waves are transmitted and received by the ultrasonic oscillator 411 provided in the housing 412. In addition, it is possible to acquire a 360° tomographic image of surrounding tissues in a blood vessel in the axial direction in a scanning manner up to an arbitrary position by pulling the entire ultrasonic catheter 1 to the proximal end side and moving the ultrasonic oscillator 411 in the longitudinal direction.

Next, a description will be given of an operation when intraluminal observation is made by using the ultrasonic catheter 1 according to the exemplary embodiment of the disclosure.

First, a priming operation for filling the ultrasonic catheter 1 with a physiological salt solution is performed prior to insertion of the sheath 2 of the ultrasonic catheter 1 into the lumen. By performing the priming operation, air inside the ultrasonic catheter 1 is removed and air entering into a lumen such as a blood vessel is prevented.

In order to perform the priming operation, the hub 31 is drawn to a hand side of a user to the maximum extent, while the male connector section 352 of the second connector 35 is connected to the female connector 372 of the unit connector 37 in the liquid tight manner. That is, a state where the inner tube 34 is drawn out from the outer tube 32 to the maximum extent (see FIG. 4) is attained, and the physiological salt solution is poured via equipment such as a tube which is connected to the port 311 of the hub 31 though not shown in the drawing, a three-way stopcock, a syringe barrel, and the like by using the syringe barrel or the like. The sheath 2 is filled with the physiological salt solution thus introduced from the hub 31. If the ultrasonic catheter 1 is completely filled with the physiological salt solution, the physiological salt solution comes out from the priming port 231 formed in the filling fluid inlet and outlet path member 23 (see FIG. 3) of the sheath 2. Based on such an event, filling with the physiological salt solution is confirmed. By performing this priming operation, it is possible to remove the air in the ultrasonic catheter 1 and prevent air from entering a lumen.

Next, as shown in FIG. 2, the ultrasonic catheter 1 is coupled to the external drive apparatus 7 which is covered with a sterilized bag (not shown) made of polyethylene. That is, the joint 50 (see FIG. 5) of the hub 31 of the ultrasonic catheter 1 is connected to the joint connection section 712 of the drive unit 71. With such an operation, it is possible to transmit and receive signals between the oscillator unit 41 and the external drive apparatus 7 and to rotate the drive shaft 42. Then, coupling is completed by fitting the unit connector 37 with the holding section 73.

Next, the hub 31 is pushed to the distal end side by moving the drive unit 71 to the distal end side along the groove rail 76 on the base table 75, and the state where the inner tube 34 is pushed into the outer tube 32 to the maximum extent is attained (see FIG. 1). The sheath 2 is inserted into a body in this state, and the insertion is stopped after the distal end of the sheath 2 passes through a target lesion.

Figure 7:
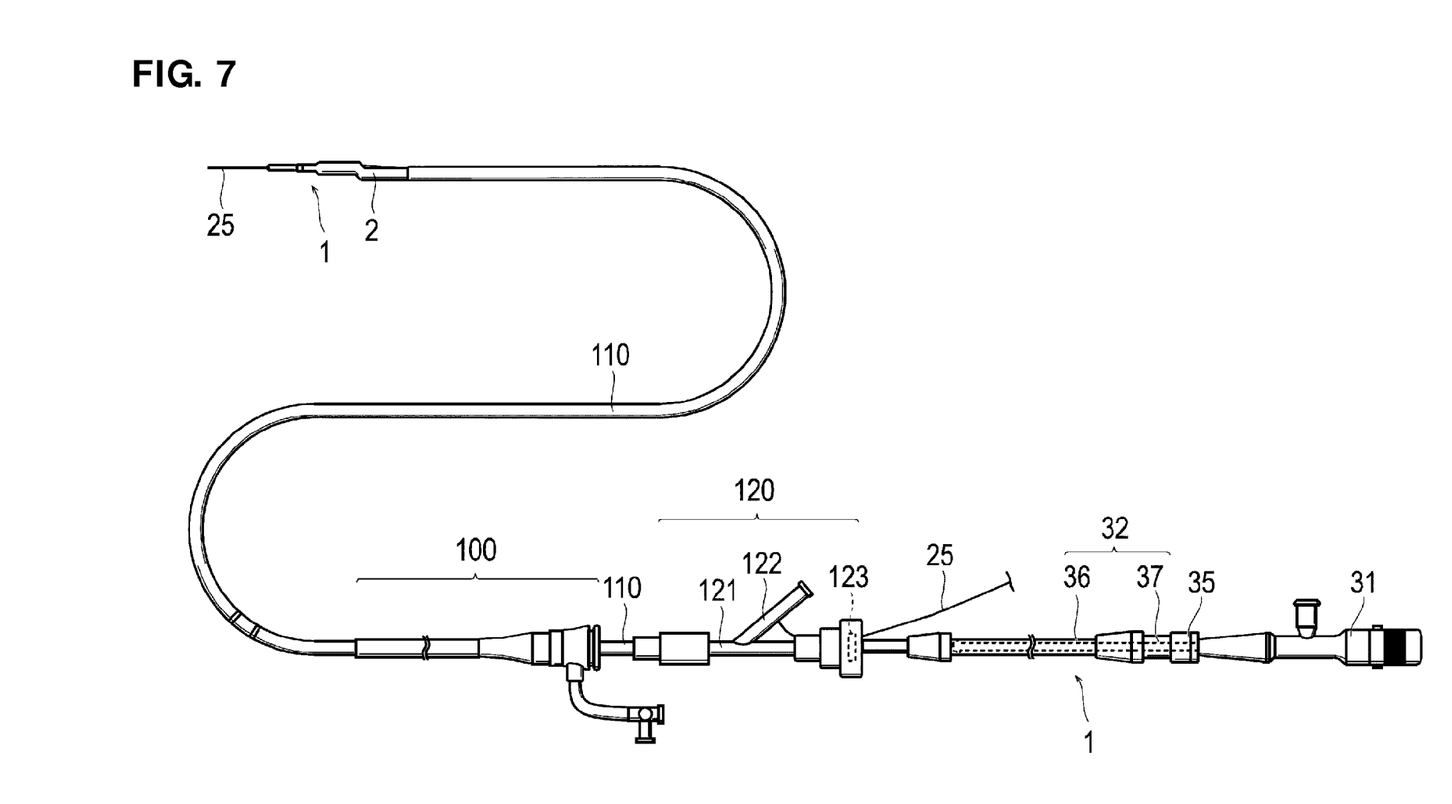
FIG. 7 is a planar view showing the ultrasonic catheter according to the exemplary embodiment of FIG. 1 inserted into a lumen.

In a case where the ultrasonic catheter 1 is inserted into a coronary artery of a heart, for example, an introducer sheath 100 is indwelled in a crural artery or the like by a Seldinger method or the like prior to the insertion of the ultrasonic catheter 1 as shown in FIG. 7. Then, a guiding catheter 110 is inserted into the body via the introducer sheath 100, and the guiding catheter 110 is indwelled at an inlet of the coronary artery.

Thereafter, the guide wire 25 is inserted up to a targeted location in the coronary artery through the guiding catheter 110. The guide wire 25 inserted into the blood vessel is made to pass through the guide wire lumen 211 of the ultrasonic catheter 1, and the sheath 2 of the ultrasonic catheter 1 is inserted into the body through the guiding catheter 110.

A Y-shaped Y connector 120, which includes a main body section 121 in coaxial communication with the guiding catheter 110 and a side port 122 which is branched from the main body section 121, is coupled to the proximal end of the guiding catheter 110, and thus a sealing performance of a clearance section between the ultrasonic catheter 1 and the guiding catheter 110 is secured by the Y connector 120.

The ultrasonic catheter 1 is inserted into the lumen via a valve body 123 in the Y connector 120, which is connected to the proximal end side of the guiding catheter 110. A speed of the insertion to the lumen is lowered when the marking section M approaches the vicinity of the valve body 123, and the ultrasonic catheter 1 is inserted up to a target lesion to be observed along the guide wire 25.

Next, the ultrasonic catheter 1 is made to reach the target portion in the lumen, and the position of the sheath 2 is then fixed. By performing a pull-back operation while rotating the drive shaft 42 by the drive unit 71 in this state, it is possible to acquire an image in the axial direction of the lumen.

The pull-back operation can be performed by operating, via the control unit 79, the moving means 72 connected to the rear end of the ultrasonic catheter 1. The acquired data is subjected to digital processing by the control unit 79 and is displayed as image data on the display unit 78.

Then, the hub 31 is pushed again to the distal end side after the pull-back operation, and the imaging core 4 is made to advance forward. Although an operation of pulling out the ultrasonic catheter 1 from the lumen is performed thereafter, there is a possibility that a phenomenon where the guide wire 25 is bent and is separated from the ultrasonic catheter 1, namely a so-called "wire separation" may be caused by pulling the ultrasonic catheter 1 to the proximal end side due to the rapid exchange structure of the ultrasonic catheter 1 in a case where the ultrasonic catheter 1 is inserted into a curved lumen, for example. If such a phenomenon occurs and a kink in which the guide wire 25 is folded back, for example, is caused, there is a concern in that it becomes difficult to move the ultrasonic catheter 1 along the guide wire 25. In another case where the ultrasonic catheter 1 is used for checking a stent indwelled in a lumen, for example, there is a concern that the ultrasonic catheter 1 and the guide wire 25 may be caught by a strut of the stent and it becomes difficult to pull out the ultrasonic catheter 1.

Figure 8:
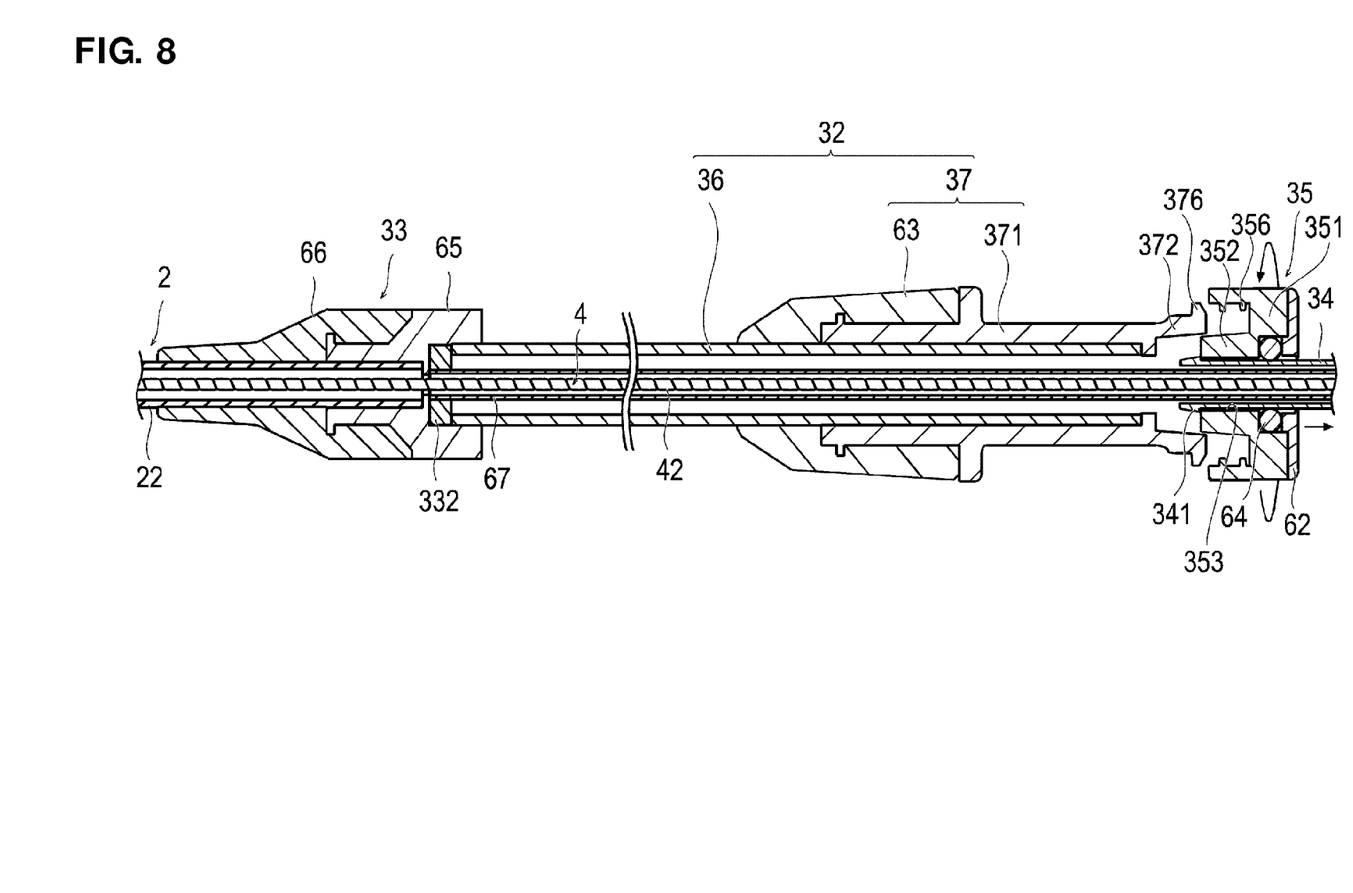
FIG. 8 is a longitudinal-direction cross sectional view showing the connection by a second connector released.
Figure 9:
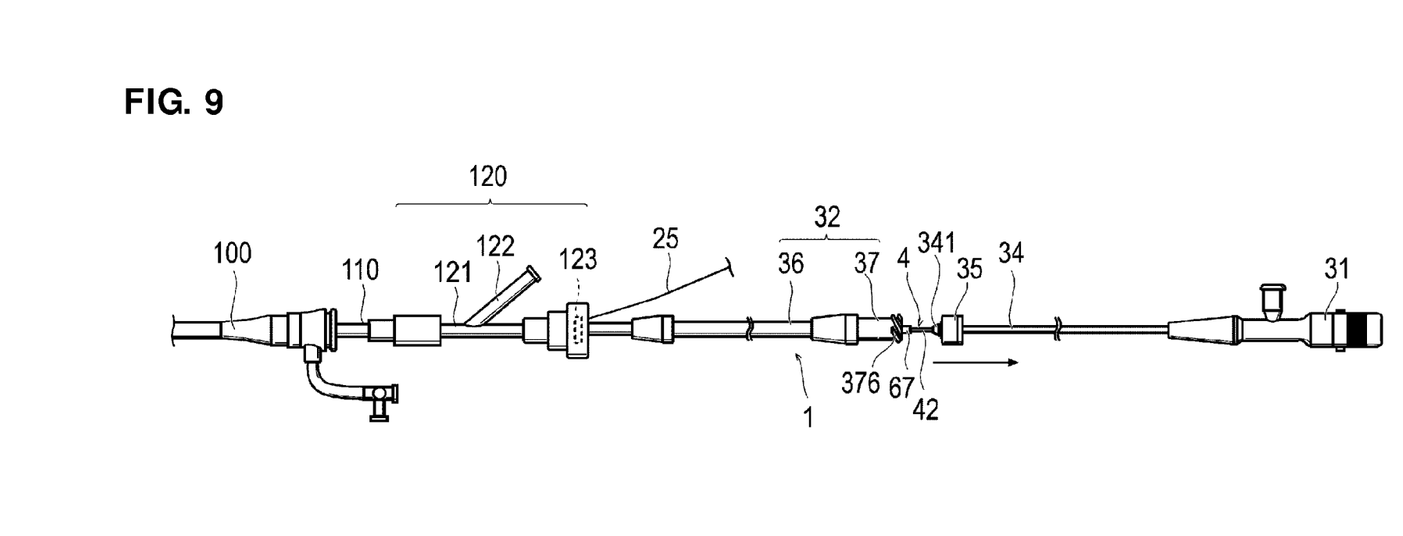
FIG. 9 is a planar view showing the connection by the second connector released.

In such a case, it is possible to disconnect the male screw section 376 from the female screw section 356 and disconnect the male connector section 352 provided in the second connector 35 from the female connector 372 provided in the unit connector 37 simply by the operator rotating the second connector 35. In addition, if the hub 31 is moved to the proximal end side in a state where the outer tube 32 is carried and fixed, the inner tube 34 and the imaging core 4 move to the proximal end side along with the hub 31 as shown in FIGS. 8 and 9, and the second connector 35 also moves to the proximal end side if the stopper 341 of the inner tube 34 is caught by the inner wall of the passing port 353 of the second connector 35. If the hub 31 is further moved to the proximal end side, the imaging core 4 is completely pulled out from the sheath 2 and the outer tube 32.

Thereafter, a separately prepared wire such as a guide wire is inserted into the lumen where the imaging core 4 is arranged and is made to reach the distal end of the sheath 2, and the sheath 2 and the guide wire 25 can be recovered to appropriate states by operating the sheath 2 and the guide wire 25 while applying force to the inside of the sheath 2 by the wire. By such an operation, it is possible to pull out the sheath 2 and the guide wire 25 from the lumen.

According to the ultrasonic catheter 1 of the exemplary embodiment disclosed here, the outer tube 32 with the female connector 372 is provided on the proximal end side of the sheath 2, the second connector 35 with the male connector section 352 which can be connected to and disconnected from the female connector 372 is provided on the proximal end side of the outer tube 32, the inner tube 34 which moves with respect to the outer tube 32 in the outer tube 32 along with the movement of the hub 31 is provided, and the stopper 341 (latch section) which cannot pass through the inside of the second connector 35 is provided at the distal end of the inner tube 34 as described above. Accordingly, it is possible to hold the inner tube 34 by the stopper 341 which is caught by the second connector 35 such that the inner tube cannot fall out, in a state where the second connector 35 is connected to the outer tube 32. Furthermore, it is possible to cause the stopper 341 of the inner tube 34 to be caught by the second connector 35, to hold the second connector 35 so as not to fall off from the inner tube 34, and to pull out the imaging core 4 from the sheath 2 by disconnecting the second connector 35 from the outer tube 32 and moving the hub 31 to the proximal end side.

In addition, according to the ultrasonic catheter 1 of the exemplary embodiment disclosed here, the second connector 35 is provided on the proximal end side of the outer tube 32 instead of the distal end, and is arranged so as to be separate from the Y connector 120 during the operation. For this reason, the second connector 35 does not interfere with the guide wire 25 passing through the Y connector 120, and it becomes easier to push the guide wire 25 even when the ultrasonic catheter 1 is operated, which enhances the operability of the guide wire 25 and the ultrasonic catheter 1.

In addition, since the second connector 35 is separate from the Y connector 120, with the outer tube 32 interposed therebetween, blood flowing out from the second connector 35 is not erroneously recognized as blood flowing out from the Y connector 120, and it is possible to perform the operation while checking from which of the second connector 35 and the Y connector 120 the blood flows out from, thereby enhancing the operability.

In addition, since the second connector 35 is separate from the Y connector 120, with the outer tube 32 interposed therebetween, it becomes difficult for the blood flowing out from the second connector 35 to enter the valve body 123 provided in the Y connector 120 from the outside, which also enhances the operability.

In addition, since the male connector section 352 and the female connector 372 are screw-type connectors fixed by the female screw section 356 and the male screw section 376, it is possible to easily perform connection and disconnection while exhibiting a high sealing performance, which enhances the operability.

In addition, if the proximal end side of the unit connector main body 371 has a female luer taper connector shape, it is possible to perform the operation while stopping the blood flowing out from the outer tube 32 by connecting a commercially available homeostatic device (such as a Y connector).

Further, since the seal member 64 is provided inside the second connector 35 and is brought into contact with the outer circumferential surface of the inner tube 34 so as to be slidable, it is possible to move the inner tube 34 with respect to the second connector 35, to facilitate connection and disconnection by enabling the second connector 35 to rotate independently from both the outer tube 32 and the inner tube 34, and to suppress leakage from a portion between the second connector 35 and the inner tube 34. The second connector can be manually disconnected tool free.

In addition, since the ultrasonic catheter 1 according to the exemplary embodiment can be disconnected at the second connector 35, it is possible to provide a side of the sheath 2 and the outer tube 32, which is inserted into a lumen and can be created at a relatively low cost, as disposable components, and to provide an expensive side of the hub 31 and the inner tube 34, which includes the image core 4, as reusable components. In addition, since the side of the sheath 2 of the ultrasonic catheter 1 according to the exemplary embodiment can be disconnected by the second connector 35, it is possible to replace the sheath 2 with another sheath with different thickness, a different monorail length, or the like in accordance with a particular situation where the ultrasonic catheter 1 is being used.

The disclosure herein is not limited to the aforementioned exemplary embodiment, and various modifications can be made by those skilled in the art within a scope of the technical idea of the disclosure. For example, although the disclosure was applied to an ultrasonic catheter as described in the aforementioned exemplary embodiment, the disclosure can be applied to an optical probe for a diagnostic apparatus (OCT catheter) utilizing light such as an optical coherent tomography apparatus or an optical frequency domain imaging apparatus for diagnosis, a telescope system, or the like and can be applied to any catheter as long as the catheter has a tubular body.

Figure 10:
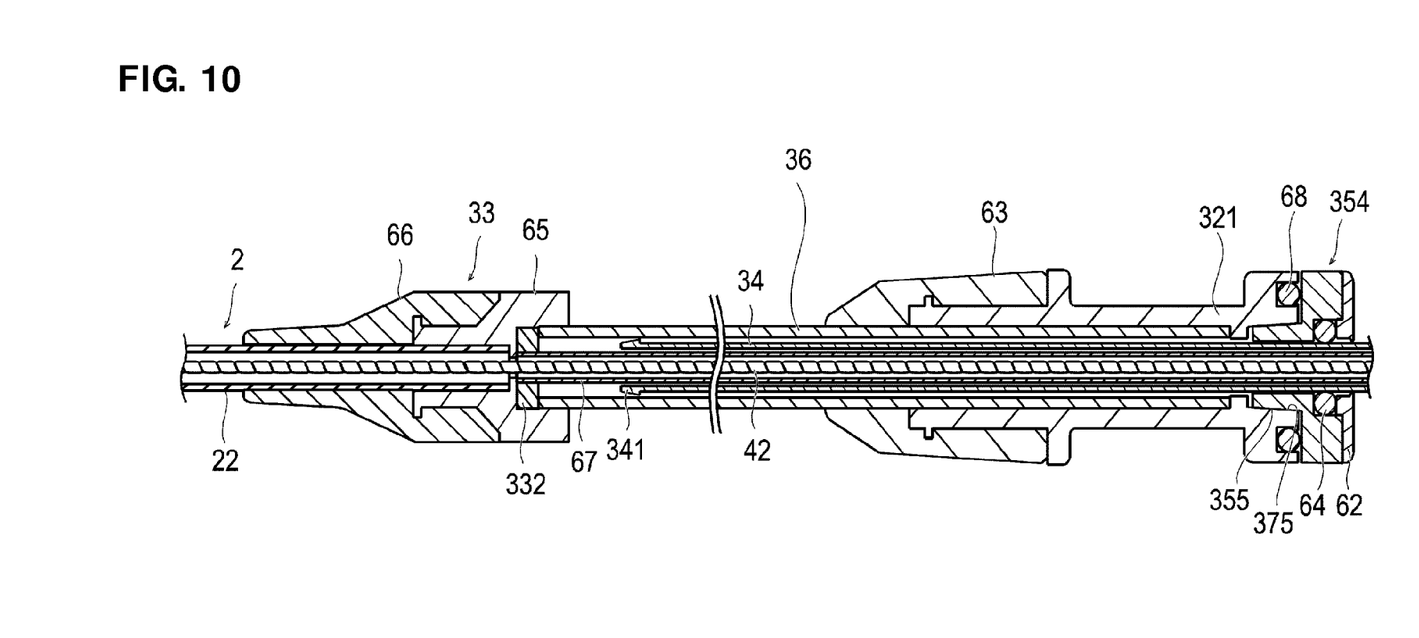
FIG. 10 is a longitudinal-direction cross sectional view showing a unit connector and a relay connector in a modified example of the ultrasonic catheter according to the exemplary embodiment of the disclosure.

In addition, although the female connector 372 is provided on the side of the outer tube 32 and the male connector 352 is provided on the side of the second connector 35 in the exemplary embodiment, the male connector may be provided on the side of the outer tube 32 and the female connector may be provided on the side of the second connector 35. In addition, another structure may be applied as a structure for the connection of the first connector and the second connector. For example, an insertion-type luer taper structure may be employed in which a tapered male connector section 355 and the female connector section 375 are provided and connection can be made merely by insertion thereof, as in the modified example shown in FIG. 10. Since there is a possibility that a priming solution and blood leak more easily in the case of the insertion type than in the case of the screw type, it is preferable to provide a second O-ring 68 (sealing member) interposed and compressed between the second connector 354 and the outer tube 321 when the second connector 354 is connected to the outer tube 321. In addition, it is a matter of course that such a second O-ring 68 can be used even in the case of the screw type as shown in FIG. 6. In addition, the structure for the connection may be the screw type or the insertion type which are not the luer taper structure. In such a case, since there is a possibility that the sealing performance deteriorates as compared with the case of the luer taper structure, it is preferable to provide the same configuration as that of the aforementioned second O-ring 68 (see FIG. 10).

Further, the proximal end of the sheath 2 can be utilized as the protecting tube 67 without any change. In such a case, it is not necessary to provide the proximal end sealing member 62 and the seal member 64 if a seal member is provided at the proximal end of the sheath 2 at a space from the inner tube. Moreover, the proximal end of the sheath 2 can also be used as the outer tube 32 without any change. Since the inner tube 34 is directly inserted into the sheath 2 in this case, it is not necessary to provide the relay connector 33, the outer tube main body 36, and the cover member 63. Furthermore, since the inner hollow of the sheath 2 is narrow, there is no risk that the drive shaft becomes bent in the sheath 2, and therefore, it is not necessary to provide the protecting tube 67.

The detailed description above describes a catheter. The invention is not limited, however, to the precise exemplary embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
    a sheath configured to be inserted into a lumen;
    a drive shaft configured to be removably inserted into the sheath and to deliver a mechanical drive force;
    an image information acquiring unit which is fixed to a distal end of the drive shaft and acquires image information;
    a hub which moves while holding the drive shaft and thereby moves the drive shaft in an axial direction of the sheath;
    an outer tube which is provided on a proximal end side of the sheath and includes a first connector at a proximal end thereof;
    a second connector, the second connector being configured to be connected to and disconnected from the first connector, on a proximal end side of the outer tube; and
    an inner tube which is provided on a distal end side of the hub, moves with respect to the outer tube in the outer tube along with the movement of the hub, and includes a latch section with an enlarged outer diameter provided at a distal end thereof, the latch section passing through the first connector;
    wherein the second connector includes a passing port which can receive the inner tube, and the passing port has an opening diameter which does not allow the latch section with the enlarged outer diameter to pass therethrough.

2. The catheter according to claim 1,
    wherein the first connector and the second connector are screw-type connectors.

3. The catheter according to claim 1,
    wherein the second connector includes a seal member which is brought into contact with an outer circumferential surface of the inner tube so as to be slidable.

4. The catheter according to claim 1,
    wherein the hub includes a port for inletting a fluid and for air venting.

5. The catheter according to claim 1,
    further comprising a relay connector which connects a portion between the outer tube and the sheath.

6. The catheter according to claim 5,
    wherein the outer tube includes an outer tube main body on a distal end side which is fixed to the relay connector.

7. The catheter according to claim 1,
    wherein the sheath includes a sheath distal end, a sheath tube, and a filling fluid inlet and outlet path member.

8. The catheter according to claim 7,
    wherein the filling fluid inlet and outlet path member includes a priming port formed therein such that a fluid filling the sheath tube flows to the outside.

9. The catheter according to claim 7,
    wherein the image formation acquiring unit is disposed to slide in an axial direction of the sheath.

10. The catheter according to claim 9,
    wherein the image formation acquiring unit includes an oscillator unit, the oscillator unit being rotated by the drive shaft.

11. The catheter according to claim 10,
wherein, when the inner tube is inserted to a maximum extent within the outer tube, a distal end portion of the inner tube reaches a vicinity of a distal end portion of the outer tube.

12. The catheter according to claim 11,
wherein, when the inner tube is withdrawn to a maximum extent from the outer tube, the latch section engages the second connector to prevent separation of the inner tube from the outer tube.

13. The catheter according to claim 1,
wherein the first connector includes a unit connector main body and a cover member.

14. A coronary catheter comprising:
an introducer sheath configured to be indwelled in a coronary artery;
a guiding catheter configured to be inserted into a lumen through the introducer sheath;
an ultrasonic catheter including a sheath configured to be inserted into the lumen through the guiding catheter;
a drive shaft configured to be inserted into the sheath and to deliver a mechanical drive force;
an image information acquiring unit which is fixed to a distal end of the drive shaft and acquires image information;
a Y-shaped connector coupled to a proximal end of the guiding catheter, the Y-shaped connector having a side port and a valve body, wherein the ultrasonic catheter is inserted into the guiding catheter through the valve body;
a hub which moves while holding the drive shaft and thereby moves the drive shaft in an axial direction of the sheath;
an outer tube which is provided on a proximal end side of the sheath and includes a first connector at a proximal end thereof;
a second connector, configured to be connected to and disconnected from the first connector, on a proximal end side of the outer tube; and
an inner tube which is provided on a distal end side of the hub, moves with respect to the outer tube in the outer tube along with the movement of the hub, and includes a latch section with an enlarged outer diameter provided at a distal end thereof;
wherein the second connector includes a passing port which can receive the inner tube, and the passing port has an opening diameter which does not allow the latch section with the enlarged outer diameter to pass therethrough;
wherein the outer tube is disposed between the second connector and the Y-shaped connector.

15. The coronary catheter according to claim 14,
wherein the first connector and the second connector are screw-type connectors.

16. The coronary catheter according to claim 14,
wherein the second connector includes a seal member which is brought into contact with an outer circumferential surface of the inner tube so as to be slidable.

17. The coronary catheter according to claim 14,
wherein the hub includes a port for inletting a fluid and for air venting.

18. The coronary catheter according to claim 14,
further comprising a relay connector which connects a portion between the outer tube and the sheath.

19. The coronary catheter according to claim 18,
wherein the outer tube includes an outer tube main body on a distal end side which is fixed to the relay connector.

20. The coronary catheter according to claim 14,
wherein the sheath includes a sheath distal end, a sheath tube, and a filling fluid inlet and outlet path member.

21. A catheter comprising:
a sheath configured to be inserted into a lumen;
a drive shaft configured to be inserted into the sheath and to deliver a mechanical drive force;
an image information acquiring unit which is fixed to a distal end of the drive shaft and acquires image information;
a hub which moves while holding the drive shaft and thereby moves the drive shaft in an axial direction of the sheath;
an outer tube which is provided on a proximal end side of the sheath and includes a first connector at a proximal end thereof, the first connector including a connector main body and a cover member, a proximal end of the connector main body having a tapered connection with a screw section formed in an outer circumference of the tapered connection;
a second connector having a tapered connector section and a screw section formed in an outer circumference of the tapered connector section, the second connector being configured to be connected to and disconnected from the first connector, on a proximal end side of the outer tube; and
an inner tube which is provided on a distal end side of the hub, moves with respect to the outer tube in the outer tube along with the movement of the hub, and includes a latch section with an enlarged outer diameter provided at a distal end thereof,
wherein the second connector includes a passing port which can receive the inner tube, and the passing port has an opening diameter which does not allow the latch section with the enlarged outer diameter to pass therethrough.

* * * * *